(12) United States Patent
Newkome et al.

(10) Patent No.: US 7,368,512 B2
(45) Date of Patent: May 6, 2008

(54) DETECTION AND FUNCTIONALIZATION OF DENDRIMERS

(75) Inventors: George Newkome, Temple Terrance, FL (US); Charles N. Moorefield, Tampa, FL (US); Claus Weis, Pfeffingen (CH)

(73) Assignee: University of South Florida, Tampa, FL (US)

( * ) Notice: Subject to any disclaimer, the term of this patent is extended or adjusted under 35 U.S.C. 154(b) by 315 days.

(21) Appl. No.: 10/752,290

(22) Filed: Sep. 14, 2004

(65) Prior Publication Data

US 2005/0008571 A1    Jan. 13, 2005

Related U.S. Application Data

(63) Continuation of application No. 09/159,560, filed on Sep. 23, 1998, now abandoned.

(60) Provisional application No. 60/059,820, filed on Sep. 23, 1997.

(51) Int. Cl.
C08F 283/04 (2006.01)

(52) U.S. Cl. ............... 525/420; 436/106; 436/129; 525/432

(58) Field of Classification Search ............... 436/106, 436/129; 525/420, 432
See application file for complete search history.

(56) References Cited

OTHER PUBLICATIONS

Sakae et al, Michrochem. J., 49(2-3), p 355-361 (1994).*
Nakamura, Busnseki, (1), p 66-68 (1989).*
Nimura, Anal. Lett., 13(A3), p 191-202 (1980).*

* cited by examiner

*Primary Examiner*—Bernard Lipman
(74) *Attorney, Agent, or Firm*—Kohn & Associates

(57) ABSTRACT

A method of detecting unreacted termini within a dendritic structure is achieved by exposing a dendrimer to a single generating compound capable of bonding to and tagging a deprotected but uncoupled termini. A signal generated by the signal generating compound to an otherwise uncoupled termini provides detection of the unreacted termini.

11 Claims, 1 Drawing Sheet

DETECTION AND FUNCTIONALIZATION OF DENDRIMERS

CROSS-RELATED REFERENCE SECTION

This application is a continuation application of U.S. patent application Ser. No. 09/159,560, filed Sep. 23, 1998, now abandoned, which claims the benefit of priority of U.S. Provisional Patent Application Ser. No. 60/059,820, filed Sep. 23, 1997, both of which are incorporated herein by reference.

GRANT REFERENCE

The research carried out in connection with this invention was supported in part by a grant from the National Science Foundation, (DMR-92-17331; 92-08925; 96-22609, the U.S. Army Office of Research (DAAHO4-93-0048), and NATO.

TECHNICAL FIELD

The present invention relates to dendrimer chemistry and more specifically to the detection of defects in dendrimers.

BACKGROUND OF THE INVENTION

Dendrimer chemistry is expanding at a rapid rate. Dendrimers are being adapted for pharmacological uses, industrial uses, coatings, as well as other areas where unimolecular isolar molecules can be engineered to provide specific chemical properties to a system. For example, dendrimers can be used as carriers of drugs, metals, or the like and site directed to specific low side. Dendrimers can also be used in or as coatings to, for example, impart a homogeneous layer to a substrate.

In producing dendritic macromolecules, especially those which are megatiered (four tiers and greater), there is a continued inability to determine quantitatively or qualitatively the absolute homogeneity of the resultant structures. This has lead many researchers to claim a monodisperse character of their products, since there is no way to insure monomolecular structure.

By monodisperse, it is meant that the dendrimer is defined as a mixture of closely related macromolecules within a given family. These molecules include what are considered "faults", albeit they may be to only a minimum degree.[1] A monomolecular dendrimer means herein that a perfectly defined structure of known composition, possessing no detectable faults is obtained.

In the efforts to determine the existence of faults in dendritic molecular domains, there has been an inability to effect chromatographic separation of the macromolecular components. This has been coupled with the general lack of resolution of spectral analysis associated with current instrumentation. This situation has lead researchers to a quest for chemical methods to circumvent this quandry.

It has been recognized in accordance with the present invention that most divergent procedures for obtaining dendritic macromolecules are two step coupling-deprotecting sequences. It has therefore been recognized, in accordance with the present invention, that it is feasible to analyze those uncoupled termini, the uncoupled termini being referred to as "loose ends". These uncoupled termini are effectively loose ends in that they represent the heterogeneity of the otherwise homogeneous molecule. The loose ends represent heterogeneity in that they are reactive components or at least capable of reactivity which is differentially effected relative to the remainder of the macromolecule. In other words, the present invention recognizes the uncoupled termini as areas of reactivity which can be differentiated from the remainder of the macromolecule.

Illustrative of the above chemically defined situation wherein dendritic molecules have uncoupled termini, FIG. 1 shows the introduction of faults during the creation[2] of a dendritic polyamido-based dendritic family. This family is chemically described as Z-Cascade:methane[4]:(3-oxo-6-oxa-2-azahaptylidene):(3-oxo-2-azapent-ylidyne)":propanoic acid.[3] Practically, this series of dendritic molecules is formed by a repetitive treatment of a polycarboxylic acid with "Behera's Amine"[4] by a peptide coupling procedure[5], followed by quantitative hydrolysis with formic acid to afford higher generations. The purity or monodispersed character of each resultant macromolecule was monitored by normal spectroscopic and analytical procedures. A problem was reached beyond the third generation of the macromolecule. The analytical procedures normally used in the prior art were less definitive as to the monodispersity and, in particular, "unimolecular" character of the larger products. This general observation is consistent with all current divergent procedures used for generating dendritic macromolecules.

In order to circumvent the above limitations relating to the inability of confirming unimolecular character of larger products, the inventors of the present invention reported the creation of bis-dendrimers[6]. These bis-dendrimers were assembled by the coupling of two totally characterized halves through a metal ion connectivity. The presence of the metal's content and oxidation state was then ascertained electro-chemically.

The present invention provides a novel application of traditional qualitative analysis procedures[7] to evaluate the presence of residual termini which fail to react during a coupling procedure. Hence, the present invention provides a method of detecting unreacted termini within a dendritic structure. Likewise, the present invention provides a method of characterizing the termini of dendrimers as well as determining the monodisperse versus monomolecular character of a dendrimer. Such methods find utility in characterizing dendrimers made by diverse methods as the characterization procedure is not dependent upon the method by which the dendrimers were constructed. Rather, the inventor procedure can be utilized for the characterization of dendrimers made by any procedure which is divergent in character.

SUMMARY OF THE INVENTION

In accordance with the present invention, there is provided a method of detecting unreacted termini within a dendritic structure by exposing a dendrimer to a single generating compound capable of binding to and tagging a deprotected but uncoupled termini. A signal generated by the signal generating compound bound to an otherwise uncoupled termini is detected as an indication of the presence of unreacted termini.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
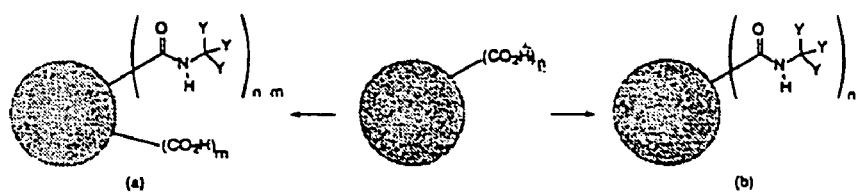
FIG. 1 is a schematic representation of a general faulted and idealized divergent growth pattern to a monodispersed (a) and monomolecular (b) dendrimer, respectively.

Generally, the present invention provides a method of detecting unreacted termini within a dendritic structure by the general steps of exposing a dendrimer to a signal generating compound capable of binding to and tagging a deprotected but uncoupled termini and then detecting a signal generated by the signal generating compound bound to an otherwise uncoupled termini as an indication of the unreacted termini.

By dendritic structure, it is meant that a macromolecule has a central core with arbor-like extensions extending therefrom. Consistent with the present invention, these molecules can have a single carbon core with branches extending therefrom or a multi-molecular core likewise having branches extending therefrom. These branches can be made by a tiered synthetic approach wherein layers of branches are built layer upon layer upon the molecule.

As stated above, there has been a quest for pure, homogeneous dendrimers. Likewise, there has been a quest for an analysis of the heterogeneity of dendrimers and hyperbranched polymers. The present invention provides such a quality control which can be used to detect unreacted termini in such dendrimers and hyperbranch polymers.

The terms "coupling" and "deprotection" are common terms in the art and have been used extensively as steps in dendritic chemistry[8] Basically, the protected termini are those terminis unreactive in a millieu. Deprotection presents reactive termini, such as carboxyl groups, amines, alcohols, thiols, and functionality with acidity protons which can be reactive in the millieu of the chemical system. In fact, during the dendritic synthetic process, such reactor groups are used in the tiering synthetic process. As discussed above, any dendritic processes do not yield purely totally reactive dendritic systems. The present invention takes advantage of these unreacted, uncoupled termini and effectively "tags" the termini.

The signal emitting compounds can be selected from the group of fluorescence emitters, radiation emitters, visible light emitters, polyaromatic, polyheteroaromatic conjugated alkenes and alkynes. Preferably, fluorescence emitting compounds can be used such that detections of the fluorescent signal can be a qualitative indication of unreacted termini. Fluorescence compounds can be used to detect carboxylic acids.

For example, preferred compounds, 9-anthryldiazomethane can be used to form ester bonds with carboxylic acid termini. This diazomethane is preferred as it is able to detect internally terminated carboxylic acids, even in the presence of other hydrogen bonding moieties. Other fluorescence compounds, such as fluoroscene-thioisocyanate can be used for the detection of internally terminated aminomoieties. Hence, various other functional group sensitive reagents can be useful to probe the structural integrity of various dendritic and polymolecular structures. Also, such compounds can be used to bond with the termini through various linkages, such as the ester linkage between the diazomethane compound and carboxylic acids as well as other linkages, such as urea, carbonate, ester, amide, ether, thioether, alkene, alkyne, alkane, benzylic and carbonoid.

The fluorescence emitting compounds can be selected from the group consisting essentially of anthracenes; quinonoids, β-hydroxyazo dyes, phthalocyanenes, bipyridines, terpyridines, polycyclic aromatic and polycyclic heteroaromatic to mention but a few.

The present invention can be utilized for various characterizing operations. For example, as stated above, the present invention finds utility in detecting unreacted termini within a dendritic structure. Hence, a qualitative determination can be made as to whether a product of a dendritic synthesis is monodispersed or monomolecular. Likewise, the termini which are unreacted within a dendrimer, which may be intentional or unintentional, can be characterized based on their binding to functional group sensitive reagents. In other words, the binding of the 9-anthryldiazo methane compound is an indication of carboxyl groups which are free termini whereas binding of fluoroscene thioisocyanate is a qualitative determination of the existence of amine termini. Thusly, the present invention can be used to characterize the chemical nature of the uncoupled or loose ended termini and otherwise uncharacterized dendritic structure.

EXPERIMENTAL EXAMPLES

Figure 2:
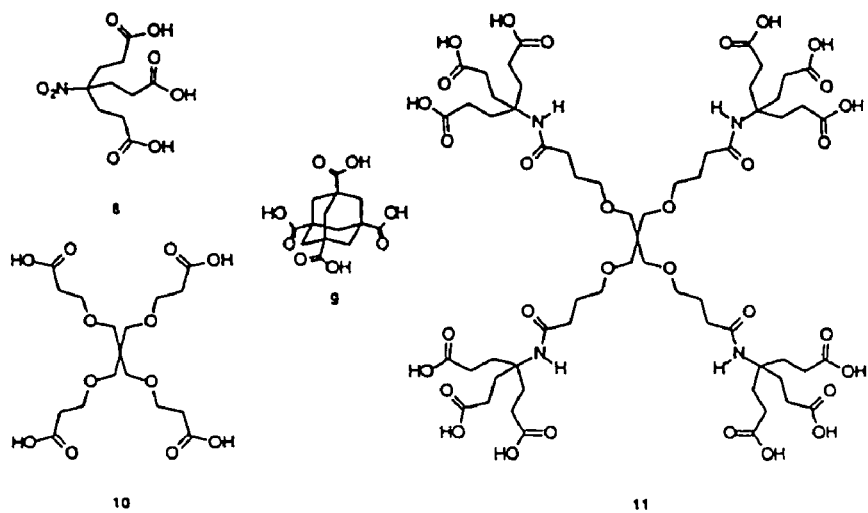
FIG. 2 is a representation of polyacid building blocks and cores.

A series of polyacids were initially utilized to test the viability of the trapping procedure. Although the triacid 8 (FIG. 2) was readily available,[4] since it is the precursor to the molecular building block "Behera's Amine", the preparation (Scheme 1) of triacid 5 was undertaken to evaluate the differences in the steric environment in the trapping step. Diethyl malonate (3) was allowed to react with 2 equiv of acrylonitrile[9] in anhydrous liquid ammonia to give (75%) the bis-Michael addition product 4, which when refluxed in concentrated hydrochloric acid gave (46%) the desired colorless triacid 5, whose structure was easily determined ($^{13}$C NMR) by the peaks at 174.7 and 176.9 ppm for the two different carboxyl groups. Interestingly, saponification of 4 at 25° C. afforded (ca. 60%) the moderately stable diacid 6, which was further hydrolyzed to the penetane-1,3,3,5-tetracarboxylic acid (7) using an ethanolic KOH solution containing 30% hydrogen peroxide. The related four-directional tetracarboxylic acids 9[10] and 10[4] have been previously described.

The white crystalline hexacarboxylate 12 was prepared (97%) from glutaroyl chloride with 2 equiv of "Behera's Amine" (Scheme 2). The structure 12 was established by the first-order NMR patterns and was readily converted to the corresponding "arboric acid" (13). Again the NMR data for 13 fully support the structural assignments. The preparation and structural characterization of the dodecacarboxylic acid 11 as well as other members of this Z-Cascade:methane[4]:(3-oxo-6-oxa-2-azaheptylidene):(3-oxo-2-azapentylidene)": propanoic acid family have been reported[2] elsewhere.

In order to ascertain the ability of diazomethane 2 to detect internally terminated carboxylic acids even in the presence of other hydrogen bonding moieties, the treatment of tetraacyl chloride 14 with the extended building block 15 afforded dendrimer 16, which upon deprotection and treatment with "Behera's Amine" using DCC and 1-HOBT conditions afforded the 36-dendrimer 17, contaminated with 17*, which, as ascertained by MALDI-TOF MS data [(M+Na)$^+$–NHC—(CH$_2$CH$_2$CO$_2$C(CH$_3$)$_3$; m/z 6553.1] possesses one residual, internal-terminated carboxylic acid moiety resulting from incomplete amidation (Scheme 4). Realizing the presence of 17*, the mixture can be readily driven to complete conversion under the above conditions.

Treatment of a carboxylic acid moiety with 9-anthryldiazomethane (2) in anhydrous diethyl ether afforded a high yield of the corresponding acetate Simply, when acetic acid was subjected to 2, the 9-anthrylmethyl acetate was generated in 100% yield. In general, the polyacids were treated with 9-anthryldiazomethane (2) under similar conditions in ether or THF to give the corresponding polyester (see Table 1). All new compounds were fully characterized by their spectral and analytical data. Limited solubility of the larger polyacids in these ethereal solvents was not problematic due to the increasing solubility of the esterified intermediates and products as the reactions proceeded.

Figure 3:
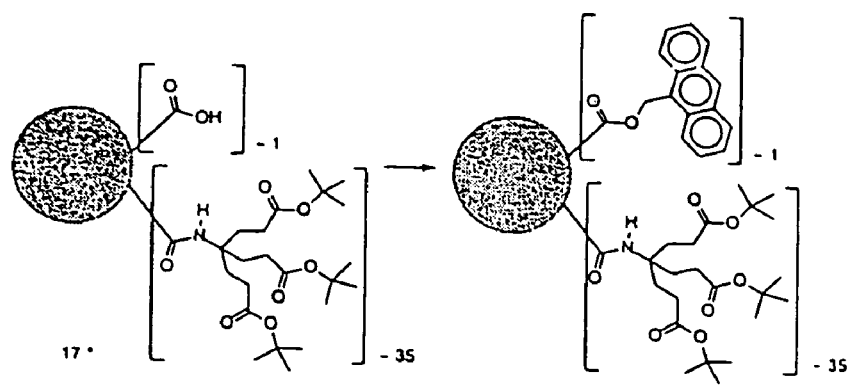
FIG. 3 is a pictorial representation of the detection procedure of the present invention using 9-anthryldiazomethane for free carboxyl moieties within a spherical dendrimer.

When the corresponding, fully substituted "monomolecular" dendrimers were treated with diazoanthracene 2, no fluorescence spectrum for the anthracene moiety was detected; however use of the "monodisperse" sample, shown by MS to be less than perfect, such as 17*, afforded a notable fluorescence (FIG. 3). Thus, this simple esterification analysis (e.g., of the 36- and 108-Cascade ester families[2]) can be readily used to detect the presence of traces (<1%) of imperfection within a given sample even when standard analytical methods, such as NMR, fail; lacking any detectable fluorescence, after treatment with anthracene 2, supports the monomolecular nature of the samples.

On the basis of the analyses of the fluorescence data (Table 2) of the above series of polyacids, there does not appear to be any linear relationship between $\epsilon_{max}$ values and the number of anthryl moieties in a given molecule. For example, comparison of the $\epsilon$ values of the excitation spectra of 18 ($\epsilon$=3124) possessing only a single anthryl unit with that of 23 ($\epsilon$=11090) having four such substituents indicates that a quantitative analysis is not guaranteed; thus, this simple procedure is only a qualitative tool to evaluate the monomolecular vs mono (poly)disperse nature of the dendritic material.

The following is a more detailed description of the syntheses utilized exemplifying the present invention:

Experimental Section

General Comments. All melting points were taken in open capillary tubes and are uncorrected. The $^1H$ and $^{13}C$ NMR spectra were recorded at 80.06 and 20.08 MHz, respectively, in $DCCl_3$ solutions, except where noted. Deuterated solvent residues were used as internal solvents [$CHCl_3$ 7.27 ($^1H$) and 77.0 ($^{13}C$) ppm; $Me_2SO$, 2.49 ($^1H$) and 39.5 ($^{13}C$) ppm], and chemical shift values ($\delta$) are reported in ppm downfield from tetramethylsilane. Infrared spectra (IR) were recorded on an IBM IR/38 Fourier transform infrared spectrophotometer. Quarts cuvettes were used for the UV ($\lambda_{max}$, $\epsilon$) and the fluorescence spectra (L=1 cm) run in $CH_2Cl_2$ having a molarity of 200 μmol at 22.5° C. The UV spectrophotometer was from UVIKON-KONTRON, Zurich, Switzerland. Elemental analyses were conducted by M-H-W Laboatories (Phoenix, Ariz.). Unless otherwise noted, all reagents and solvents utilized were of reagent grade and no further purification was undertaken.

Reagents. (a) 9-Anthryldiazomethane (2) was prepared from 9-anthrylmethanol by the procedure of Nakaya et al.[11]

(b) 1,5-Dicyano-3,3'-bis(ethoxycarbonyl)pentane (4). To a stirred solution of diethyl malonate (3; 32 g, 200 mmol) in liquid $NH_3$ (300 mL) was added acrylonitrile (21.2 g, 400 mmol) at −55 to −60° C. over 10 min. The temperature was maintained for 30 min. and then allowed to increase to 25° C. The resultant white crystals were recrystallized (EtOH, 50 mL) to give (75%) the desired diester 4: 40 g; mp 62° C. (lit.[12] mp 62° C.); $^1H$ NMR δ 1.29 (t, J=7 Hz, 6H, $CH_3$), 2.24 (t, J=7 Hz, $CH_2CN$, 4H), 2.46 (t, J=4 Hz, $CH_2CH_2CN$, 4H), 4.25 (q, J=7 Hz, $CH_3CH_2$, 4H); $^{13}C$ NMR δ 12.78 ($CH_2CH_2CN$) 13.68 ($CH_2CH_3$), 29.20 ($CH_2CH_2CN$), 55.36 (4C), 62.15 ($OCH_2$), 118.45 (CN), 168.91 ($CO_2$).

(c) 1,5-Dicyano-3,3-dicarboxypentane (6). A solution of 1,5-dicyano-3,3'-bis(ethoxycarbonyl) pentane (4; 5.32 g, 20 mmol) with KOH (1.15 g, 20 mmol) in EtOH (60 mL) and water (15 mL) was stirred at 25° C. for 24 h. The solution was concentrated in vacuo, then water (150 mL) was added and the solution was extracted with ether (2×30 mL). The aqueous solution was acidified with HCl and extracted with ether. The solvent was dried ($MgSO_4$) and concentrated in vacuo to afford (57%) the desired diacid 6, as colorless crystals: 2.4 g; mp 152° C.; $^1H$ NMR (DMSO-$d_6$) δ 2.07 (t, J=8 Hz, $CH_2CN$, 4H); 2.46 (t, J=8 Hz, $CH_2CH_2$, 4H), 12.0 (br, $CO_2$ H, 2H); $^{13}C$ NMR (DMSO-$d_6$) 12.44 ($CH_2CN$), 27.66 ($CH_2$—$CH_2CN$), 55.45 (4C), 120.19 (CN), 171.25 ($CO_2$).

(d) 1,3,5-Pentanetricarboxylic Acid (5). A suspension of 1,5-dicyano-3,3'-bis(ethoxycarbonyl)pentane in concentrated HCl (50 mL) was refluxed for 48 h. The solution was concentrated in vacuo then diluted with water (50 mL) and reconcentrated in vacuo to give a solid, which was recrystalized (MeCN) to give (46%) this triacid, as a colorless solid: 1.42 g; mp 115-116° C.; $^3C$ NMR (DMSO-$d_6$) δ 27.3 ($CH_2$—$CO_2H$), 32.0 ($CH_2CH_2CO_2H$), 43.9 (4C), 174.7 ($CH_2CO_2OH$), 176.9 ($CO_2H$). Anal. Calcd for $C_8H_{12}O_6$: C, 47.05, H, 5.82. Found: C, 47.06, H, 5.92.

(e) 1,3,3,5-Pentanetetracarboxylic Acid (7). To a solution of 1,5-dicyano-3,3'-bis(ethoxycarbonyl)pentane (4; 4.0 g, 15 mmol) in a mixture of EtOH (150 mL), water (50 mL), and KOH (18 g, 320 mmol), $H_2O_2$ (45 mL, 30%) was slowly added at 10-20° C., and then stirred for 45 min. at 25° C. The temperature was then increased to 60-70° C. for 20 h. After the solvent was distilled in vacuo, and concentrated HCl was added to attain the pH=1, the solution was continuously extracted with ether for 7 h. Concentration of the extract in vacuo furnished an oil, which crystallized (MeCN) on standing to afford (76%) the desired tetraacid 7: 2.71 g; mp 168-171° C.(dec.); $^{13}C$ NMR (DMSO-$d_6$) δ 27.59 ($CH_2CO_2H$), 29.48 ($CH_2CH_2CO_2H$), 55.93 (4C), 172, 84 (CCOOH), 174.28 ($CH_2CO_2H$). Anal. Calcd for $C_9H_{12}O_8$: C, 43.55; H, 4.87. Found: C, 43.80; H, 4.51.

(f) 1,3,5,7-Adamantanetetracarboxylic acid (9) was prepared according to the literature[10a] or by a more novel route from adamantanecarboxylic acid.[10b]

tert-Butyl 4,4,12,12-Tetrakis (β-carboxyethyl)-5,11-diaza-6,10-diketopentadecanoate (12). A solution of di-tert-butyl 4-amino-4-[(2-tert-butoxycarbonyl)ethyl]-1,7-heptanedioate[4] (4.14 g, 10 mmol) and $Et_3N$ (1.1 g, 10 mmol) in THF (40 mL) was added drop wise to a stirred solution of glutaryl chloride (845 mg, 5 mmol) in THF (50 mL) at 50° C. over a period of 30 min. and maintained at 50° C. for 1 h. Stirring at 25° C. was continued for 24 h, then $Et_3N·HCl$ was filtered and the THF removed in vacuo. The residue was dissolved in ether (150 mL), washed with a $NaHCO_3$ solution (5%, 20 mL) and then water (20 mL), and dried ($Na_2SO_4$). Distillation of the solvent gave (97%) the desired product 12, which was recrystallized from cyclohexane (40 mL) affording white crystals: 4.51 g; mp 116-118° C.; $^1H$ NMR δ 1.43 [s, C ($CH_3$)$_3$, 54H], 1.95 (m, $CH_2$—$CH_2CH_2$, $CH_2CH_2CO$, 14H), 2.18 (m, $CH_2CH_2CH_2$, $CH_2CH_2$—CO, 16H), 6.15 (br, NH); $^{13}C$ NMR δ 21.60 ($CH_2CH_2CH_2$), 28.24 [($CH_3$)$_3$], 29.87 ($O_2CCH_2CH_2$), 30.10 ($O_2CCH_2CH_2$), 35.84 (NHCOCH$_2$CH$_2$), 57.74 (CNHCO), 80.79 (COCO), 172.18 (NHCO), 172.96 (CO$_2$).

(h) 4,4,12,12-Tetrakis(β-carboxyethyl)-5,11-diaza-6,10-diketopentadecanoic Acid (13). A solution of hexaester 12 (3.46 g, 373 mmol) in formic acid (25 mL) was allowed to stand at 25° C. for 24 h, then the volatile products were distilled in vacuo. Water (25 mL) was added to the residue and distilled from the solution. This procedure was repeated twice yielding (95.8%) 13, as a white amorphous solid: 2.11 g; mp slow decomposition above 90° C.; $^1$H NMR (DMSO-d$_6$) δ 2.24 (d, J=7 H$_z$, 14H, CH$_2$CH$_2$CH$_2$, CH$_2$CH$_2$CO$_2$H), 2.49 (m, CH$_2$CH$_2$—CH$_2$, CH$_2$CH$_2$CO$_2$H, 16H), 7.56 (s, 2H, NH), 12.49 (s, br, 6H, CO$_2$H); $^{13}$C NMR (DMSO-d$_6$) δ 22.30 (CH$_2$CH$_2$CH$_2$), 28.30 (CH$_2$CH$_2$CO$_2$H), 29.32 (CH$_2$CH$_2$CO$_2$H), 35.83 (NHCOCH$_2$), 56.55 (C=), 172.02 (NHCO), 174.74 (CO$_2$H).

General Esterification Procedure. Tris(9-anthryl-methyl)-4-[1-(2-carboxyethyl)]-4-nitroheptanedicarboxylate (19). A solution of 9-anthryldiazomethane (2); 500 mg, 2.2 mmol) in ether (30 mL) was added to a slurry of 4-[1-(2-carboxyethyl)]-4-nitroheptanedioic acid$^{13}$ (138.5 mg, 0.5 mmol) in ether (50 mL). After the mixture was allowed to stand at 25° C. for 48 h, the solvent was removed by distillation, and the residue was crystallized from CHCl$_3$ yielding the triester 19, as yellow needles: 370 mg; UV 388.5 (3.321), 367.0 (3.728); $^1$H NMR δ 2.20 (d, J=5 Hz, 12 H, CH$_2$CH$_2$), 6.07 (s, CH$_2$, 6H), 7.26-8.44 (m, ArH, 27H); $^{13}$C NMR δ 28.50 (CH$_2$CH$_2$CO$_2$), 30.09 (CH$_2$CH$_2$CO$_2$), 59.24 (AnthCH$_2$), 91.64 (CNO$_2$) 123.72, 125.04, 125.65, 126.67, 129.02, 129.26, 130.90, 131.24 (AnthC), 171.76 (CO$_2$). Anal. Calcd for C$_{55}$H$_{45}$NO$_8$ (M=847.918): C, 77.90; H, 5.35; N, 1.65. Found: C, 77.82; H, 5.42; N, 1.67.

The related esters were purified by chromatography on silica or aluminum oxide, byproducts extracted with toluene/EtOAc, and the desired product obtained by washing the column with a mixture of CH$_2$Cl$_2$/EtOAc/MeOH. The melting points and yields are presented in Table 1.

9-Anthrylmethyl Acetate (18) was prepared (100%) from acetic acid according to the literature[11] as yellow needles: UV 348.5 (2.071), 366.5 (2.966), 386.5 (2.676); $^1$H NMR δ 1.56 (s, CH$_3$, 3H), 6.16 (s, CH$_2$, 2H), 7.49-8.53 (m, ArH, 9H); $^{13}$C NMR δ 21.24 (CH$_3$), 59.05 (CH$_2$), 124.14, 125.34, 126.43, 126.89, 129.35, 129.43, 131.27, 131.62 (ArC), 171.53 (CO$_2$).

9-Anthrylmethyl 1,5-Dicyano-3,3-pentanedicarboxylate (20): UV 388.0 (2.727), 368.0 (3.087), 350.0 (2.197); $^1$H NMR δn 2.02 (t, J=5 Hz, CH$_2$CH$_2$, 8H), 6.02 (s, CH$_2$, 4H), 7.27-8.44 (m, ArH 18H); $^{13}$C NMR δ 12.49 (CH$_2$CN), 29.31 (CH$_2$CH$_2$CN), 55.80 (4C), 60.75 (AnthCH$_2$), 118.10 (CN), 123.29, 124.65, 125.15, 126.87, 129.12, 129.71, 130.67, 131.10 (9-AnthC), 168.87 (CO$_2$). Anal. Calcd for C$_{39}$H$_{30}$N$_2$O$_4$ (M=590.64): C, 79.30; H, 5.12; N, 4.74. Found: C,79.23; H, 4.40; N, 4.70.

9-Anthrylmethyl 1,3,5-Pentanetricarboxylate (21): UV 387.0 (3.215), 366.0 (3.660), 349.0 (3.42); $^1$H NMR δ 1.59-2.17 (m, CH$_2$CH$_2$, CH, 9H); 6.02 (s, 6H, CH$_2$), 7.25-8.46 (m, ArH, 27H); $^{13}$C NMR δ 26.80 (CH$_2$CH$_2$CO$_2$), 31.52 (CH$_2$CO$_2$), 43.79 (HC=), 58.66, 58.94 (AnthCH$_2$), 172.75 (CO$_2$), 174.81 (CO$_2$). Anal. Calcd for C$_{53}$H$_{42}$C$_6$ (M=774.86): C, 82.14; H, 5.46. Found: C, 82.05; H, 5.39.

9-Anthrylmethyl 1,3,3,5-Tetrapentanetetracarboxylate (22): UV 386.0 (3.300), 369.0 (3.880), 350.0 (3.850); $^1$H NMR δ 1.86-2.03 (m, CH$_2$CH$_2$,8H), 5.80 (s, AnthCH$_2$, 4H), 5.89 (s, AnthCH$_2$, 4H) 7.24-8.15 (m, ArH, 36H); $^{13}$C NMR δ 28.40 (CH$_2$CH$_2$CO$_2$), 28.92 (CH$_2$CO$_2$), 56.22 (4C), 58.63 (AnthCH$_2$), 59.73 (AnthCH$_2$), 170.41, 172.34 (CO$_2$). Anal. Calcd for C$_{68}$H$_{52}$O$_8$ (M=997.096): C, 81.90; H, 5.26. Found: C, 81.71; H, 5.10.

9-Anthrylmethyl 1,3,5,7-Adamantanetetracarboxylate (23): UV 387.0 (3.190), 367.0 (3.546), 349.0 (3.312); $^1$H NMR δ 1.98 (s, CH$_2$, 12H), 6.04 (s, CH$_2$, 8H), 7.39-8.39 (m, ArH, 36H); $^{13}$C NMR δ 38.96 (C), 42.78 (CH$_2$), 60.21 (CH$_2$anth), 123.84, 125.02, 125.93, 126.65, 128.90, 129.12, 130.94, 131.21 (anth), 175.38 (CO$_2$). Anal. Calcd for C$_{74}$H$_{54}$O$_8$ (M=1071.17): C, 82.97; H, 5.08. Found: 82.80; H, 5.15.

Hexakis(9-anthrylmethyl), 4,4',12,12'-Tetrakis(β-carboxyethyl)-5,11-diaza-6,10-diketopentadecanoate (24): UV 364.0 (3.813); $^1$H NMR δ 1.23-1.63 (m, CH$_2$CH$_2$CH$_2$, CH$_2$—CH$_2$CO, 30H), 4.93 (s, NH, 2H), 5.96 (s, AnthCH$_2$, 12H), 7.28-8.20 (m, ArH, 54H); $^{13}$C NMR δ 21.62 (CH$_2$CH$_2$CH$_2$), 28.02 (CH$_2$CH$_2$CO$_2$), 28.83 (CH$_2$CH$_2$CO$_2$), 33.60 (COCH$_2$CH$_2$CH$_2$), 57.23 (=CNHCO), 59.11 (AnthCH$_2$), 123.96, 125.26, 126.00, 126.96, 129.33, 129.55, 131.10, 131.39 (AnthC), 171.51 (NHCO), 173.09 (CO$_2$). Anal. Calcd for C$_{115}$H$_{98}$N$_2$O$_{14}$ (M=1731.95): C, 79.74; H, 5.70; N, 1.61. Found: C, 79.70; H, 5.73; N, 1.53.

9-Anthrylmethyl 6,6-bis(carboxy-9-anthrylmethyl-2-oxabutyl)-4,8-dioxaundecane-1,11-dicarboxylate (25) was prepared from the corresponding tetraacid (10):[4] UV 388.5 (3.321), 367.0 (3.728); $^1$H NMR δ 2.22 (t, J=7.2 Hz, CH$_2$CO$_2$, 8H), 3.34 (s, CH$_2$O, 8H), 3.67 (t, J=5.7 Hz, OCH$_2$, 8H), 6.10 (s, AnthCH$_2$, 8H), 7.39-8.31 (m, ArH, 36H); $^{13}$C NMR δ 34.93 (CH$_2$CO), 44.75 (4C), 58.66 (AnthCH$_2$), 66.47 (CH$_2$O), 69.77 (OCH$_2$), 123.83, 124.93, 126.08, 126.47, 128.91, 128.99, 130.83, 131.16 (AnthC), 171.86 (CO$_2$). Anal. Calcd for C$_{77}$H$_{68}$O$_{12}$ (M=1185): C, 78.01; H, 5.74. Found: C, 78.16; H, 5.62.

12-Cascade:methane[4]:(3-oxo-6-oxa-2-azaheptylidene): 9-anthrylmethyl propanoate (26): UV 330.5 (4.000); $^1$H NMR δ 1.96 (t, J=7.2 Hz, CH$_2$CH$_2$CO$_2$, 24H), 2.22 (t, J=7.2 Hz, CH$_2$CO$_2$, 24H), 2.38 (t, J=5.7 Hz, CH$_2$CONH, 8H), 3.34 (s, CHO, 8H), 3.67 (t, J=5.7 Hz, OCH, 8H), 5.10 (s, AnthCH$_2$, 24 Hz), 7.39-8.31 (ArH, 108H); $^{13}$C NMR δ 28.16 (=CCH$_2$CH$_2$), 29.25 (CH$_2$CH$_2$CO$_2$), 36.71 (CH$_2$CONH), 44.37 (4C), 56.86 (HNC=), 58.72 (AnthCH$_2$), 66.78 (CH$_2$O), 67.52 (OCH$_2$), 123.73, 124.87, 125.93, 126.45, 128.82, 128.96, 130.73, 131.05, 170.63 (CONH), 173.13 (CO$_2$). Anal. Ccalcd for C$_{237}$H$_{208}$N$_4$O$_{32}$ (M=3624.066): C, 78.54; H, 5.78; N, 1.55. Found: C, 78.50; H, 5.74; N, 1.53.

Analysis of the Imperfect Dendrimer 17*. To a solution of 17* (200 mg, 3.05×10$^{-5}$ mol) in anhydrous diethyl ether (50 mL) was added a solution of 2 (150 mg, 6.88×10$^{-4}$ mol) in ether (20 mL). After the mixture was allowed to stand at 20° C. for 24 h, the solvent was removed in vacuo and the residue chromatographed on silica eluting with EtOAc/MeOH (1:1) to give 160 mg of the labeled ester: $^{13}$C NMR δ 27.96 (CH$_3$), 29.69, 31.37(CH$_2$CH$_2$) 57.32 (NHC≡), 58.80 (CH$_2$anth), 80.47 (CCH$_3$), 109.40, 109.73 (pyr-C3), 123.89, 125.03, 126.05, 126.62, 126.87, 129.11, 130.90, 131.22 (anthC), 140.22 (pyr-C4), 149.59, 149.91 (pyr-C2), 170.64, 171.81 (CONH), 172.66 (CO$_2$t-bu), 172.90 (CO$_2$CH$_2$anth).

In view of the above, it can be concluded that the present invention provides a method of detecting unreacted loci within macromolecules and more specifically carboxylic acid, amine, as well as other reactive internally terminated loci even in the presence of other hydrogen-bonding moieties. The present invention offers a direct rapid qualitative insight into the monomolecular versus monodisperse character of a reaction product. The present invention provides a method which is less expensive and easier to use than mass spectral analyses and which may or may not be used as an analytical tool in the quantification of these macromolecules.

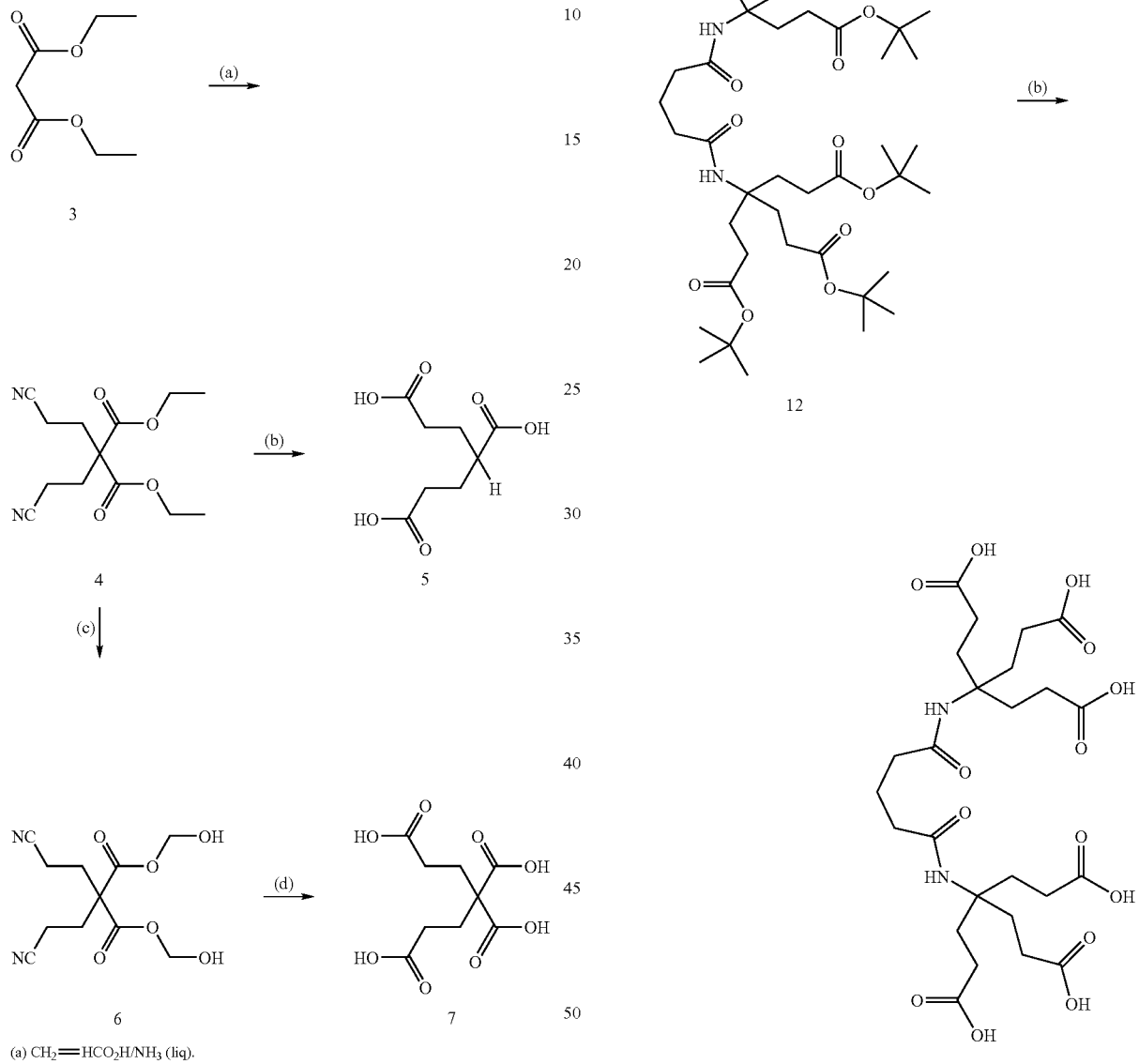

(a) $CH_2=HCO_2H/NH_3$ (liq).
(b) $HCl/\Delta$.
(c) $KOH/EtOH/25°$ C..
(d) $KOH/EtOH/H_2O_2/60-70°$ C..

(a) $H_2NC(CH_2CH_2CO_2\text{-tert-Bu})_3/NEt_3/THF/50°$ C./1 h.
(b) $HCO_2H/25°$ C./24 h.

[1]Fetters, L. J.; Thomas, E. L. Model Polymers for Material Science. In Materials Science and Technology: A Comprehensive Treatment; Cahn, R. W., Hassen, P., Keamer, E. J., Eds.; VCH Publishers: New York, 1993; Vol. 12, Chapter 1.

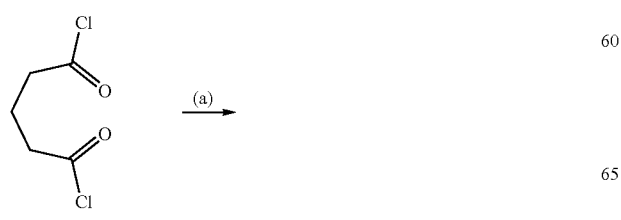

[2] Young, J. K.; Baker, G. R.; Newkome, G. R.; Morris, K. F.; Johnson, C. S., Jr. Macromolecules 1994, 27, 3464.

[3] Newkome, G. R.; Baker, G. R.; Young, J. K.; Traynham, J. T. J. Polym. Sci.: Polym. Chem. 1993, 31, 641. Newkome, G. R.; Baker, G. R. Polym. Prepr. 1994, 35,4.

[4] Newkome, G. R.; Weis, C. D. Org. Prep. Proced. Int. 1996, 28, 485, Newkome, G. R.; Behera, R. K.; Baker, G. R. Acta Crystallogr. 1994, C50, 120.

[5] Klausner, J.; Bodansky, B. Synthesis 1972, 453. De Tar, D. F.; Silverstine, R.; Rogers, F. F., Jr. J. Am. Chem. Soc. 1966, 88, 1024.

[6] Newkome, G. R.; Guther, R.; Moorefield, C. N.; Cardullo, F.; Echegoyen, L.; Perez Cordero, E.; Luftmann, H. Angew. Chem., Int. Ed. Engl. 1995, 34, 2023.

[7] Vogel, A. I. Elementary Practical Organic Chemistry. Part II. Qualitative Organic Analysis; Longmans, Green, and Co.: London, 1957. Shriner, R. L.; Fuson, R. C. The Systematic Identification of Organic Compounds, 2nd ed.; J. Wiley & Sons: New York, 1940.

[8] Newkome, G. R.; Moorefield, C. N.; Baker, G. R. Aldrichim. Acta 1992, 25, 31.

[9] Bruson, H. A. In Organic Reactions; John Wiley and Sons: New York, 1949; Vol. 5, Chapter 2, pp. 79-135.

[10] (a) Newkome, G. R.; Nayak, A.; Behera, R. K.; Moorefield, C. N.; Baker, G. R. J. Org. Chem. 1992, 57, 358. (b) Bashir-Hashemi, A.; Li, J. Tetrahedron Lett. 1995, 36, 1233.

[11] Nakaya, T.; Tomomoto, T.; Imoto, M. Bull. Chem. Soc. Jpn. 1967, 40, 693.

[12] Wakamatsu, S. J. Org. Chem. 1962, 27, 1285. Bruson, H. A.; Riener, T. W. J. Am. Chem. Soc. 1943, 65, 23.

[13] Newkome, G. R.; Moorefield, C. N.; Theriot, K. J. J. Org. Chem. 1989, 53, 5552.

What is claimed is:

1. A method of detecting unreacted termini within a dendritic structure by:
    exposing a dendrimer to a signal generating compound capable of bonding to and tagging a deprotected but uncoupled termini; and
    detecting a signal generated by the signal generating compound bound to an otherwise uncoupled termini as an indication of the unreacted termini.

2. A method as set forth in claim 1 wherein the termini is selected from the group consisting of carboxyls, amines, hydroxyls, thiols, sulfates, phosphates, and halides.

3. A method as set forth in claim 1 wherein the signal emitting compound is selected from the group consisting of fluorescence emitters, radiation emitters, conjugated alkenes, and conjugated alkynes.

4. A method as set forth in claim 3 wherein said exposing step is further defined as exposing the dendrimer to a fluorescence emitting compound, said detecting step being further defined as detecting a fluorescence signal as a qualitative indicator of unreacted termini.

5. A method as set forth in claim 4 wherein said exposing step is further defined as reacting internally terminated carboxylic acids of the dendrimer with a fluorescence emitting compound which is reactive therewith.

6. A method as set forth in claim 5 wherein said reacting step is further defined as reacting the termini and the fluorescence emitting compound through an ester linkage.

7. A method as defined in claim 6 wherein the fluorescence emitting compound is selected from the group consisting of anthracenes, β-hydroxyazo dyes, phthalocyanines, bipyridines, and terpyridines.

8. A method as defined in claim 3 wherein said fluorescence emitting compound is 9-anthryldiazomethane.

9. A method as defined in claim 3 wherein the signal emitting compound is fluorescenethiocyanate.

10. A method of characterizing the termini of a dendrimer by:
    exposing a dendrimer to a signal generating compound capable of bonding to and tagging a deprotected but uncoupled termini;
    detecting a signal generated by the signal generating compound bound to an otherwise uncoupled termini as an indication of the unreacted; and
    characterizing the termini.

11. A method of determining the monodisperse versus monomolecular character of a dendrimer by;
    exposing a dendrimer to a signal generating compound capable of bonding to and tagging a deprotected but uncoupled termini;
    detecting a signal generated by the signal generating compound bound to an otherwise uncoupled termini as an indication of the unreacted; and
    determining the monodisperse versus monomolecular character of the dendrimer.

* * * * *